United States Patent
Ng et al.

(10) Patent No.: US 9,095,651 B2
(45) Date of Patent: Aug. 4, 2015

(54) SAFETY NEEDLE ASSEMBLY AND METHODS

(75) Inventors: Chai Wayne Ng, Penang (MY); Irwan Shah Mohd Moideen, Penang (MY); Teng Sun Teoh, Penang (MY); Hang Khiang Chng, Singapore (SG)

(73) Assignee: B. Braun Melsungen AG, Melsungen (DE)

( * ) Notice: Subject to any disclaimer, the term of this patent is extended or adjusted under 35 U.S.C. 154(b) by 373 days.

(21) Appl. No.: 13/381,829

(22) PCT Filed: Jul. 15, 2010

(86) PCT No.: PCT/US2010/042173
§ 371 (c)(1),
(2), (4) Date: Mar. 20, 2012

(87) PCT Pub. No.: WO2011/011263
PCT Pub. Date: Jan. 27, 2011

(65) Prior Publication Data
US 2012/0179119 A1    Jul. 12, 2012

Related U.S. Application Data

(60) Provisional application No. 61/226,816, filed on Jul. 20, 2009.

(51) Int. Cl.
*A61M 5/158* (2006.01)
*A61M 5/32* (2006.01)
*A61M 25/06* (2006.01)

(52) U.S. Cl.
CPC ............. *A61M 5/158* (2013.01); *A61M 5/3257* (2013.01); *A61M 25/0631* (2013.01)

(58) Field of Classification Search
CPC ..................... A61M 25/0637; A61M 25/0631; A61M 5/158; A61M 25/0612; A61M 2005/1585; A61M 25/01; A61M 5/3257; A61M 5/3232
USPC .......................................... 604/171, 177, 263
See application file for complete search history.

(56) References Cited

U.S. PATENT DOCUMENTS 4,957,488 A * 9/1990 Cameron et al. .............. 604/161
5,573,512 A    11/1996 Van Den Haak
(Continued)

OTHER PUBLICATIONS

International Search Report completed and mailed Mar. 28, 2011 from corresponding International Application No. PCT/US2010/042173 filed Jul. 15, 2010 (4 pages).
(Continued)

*Primary Examiner* — Nicholas Lucchesi
*Assistant Examiner* — Weng Lee
(74) *Attorney, Agent, or Firm* — Klein, O'Neil & Singh, LLP

(57) ABSTRACT

The safety needle assembly includes a body and a wing assembly secured to the body. A grip is slidable along the exterior of the body, and a needle holder is slidable through an interior passageway in the body. The grip slides independently of the wing assembly, which is not slidable with respect to the body. The grip and the needle holder are secured to one another, so that sliding movement of the grip induces sliding movement of the needle holder. The grip and the needle holder are slidable between a distal position, in which a sharp distal tip of a needle held in the needle holder is exposed, and a proximal position, in which the sharp distal tip is not exposed.

30 Claims, 12 Drawing Sheets

(56) References Cited

U.S. PATENT DOCUMENTS

| | | | |
|---|---|---|---|
| 5,746,215 A * | 5/1998 | Manjarrez | 600/573 |
| 5,779,679 A * | 7/1998 | Shaw | 604/158 |
| 5,851,196 A * | 12/1998 | Arnett | 604/110 |
| 5,928,199 A * | 7/1999 | Nakagami | 604/171 |
| 6,878,134 B2 * | 4/2005 | Rogers et al. | 604/164.01 |
| 7,018,344 B2 * | 3/2006 | Bressler et al. | 600/573 |
| 7,037,292 B2 * | 5/2006 | Carlyon et al. | 604/110 |
| 7,294,118 B2 * | 11/2007 | Saulenas et al. | 604/110 |
| 7,322,963 B2 * | 1/2008 | Goh | 604/165.03 |
| 7,736,342 B2 * | 6/2010 | Abriles et al. | 604/192 |
| 7,914,501 B2 * | 3/2011 | Tanaka et al. | 604/198 |
| 2002/0103464 A1 | 8/2002 | Crawford et al. | |
| 2004/0236287 A1 | 11/2004 | Swenson et al. | |
| 2005/0234408 A1 | 10/2005 | Chong et al. | |
| 2008/0082054 A1 * | 4/2008 | Iwase et al. | 604/198 |

OTHER PUBLICATIONS

Written Opinion completed and mailed Mar. 28, 2011 from corresponding International Application No. PCT/US2010/042173 filed Jul. 15, 2010 (3 pages).

Preliminary Report on Patentability completed Jan. 24, 2012 and mailed Feb. 2, 2012 from corresponding International Application No. PCT/US2010/042173 filed Jul. 15, 2010 (6 pages).

* cited by examiner

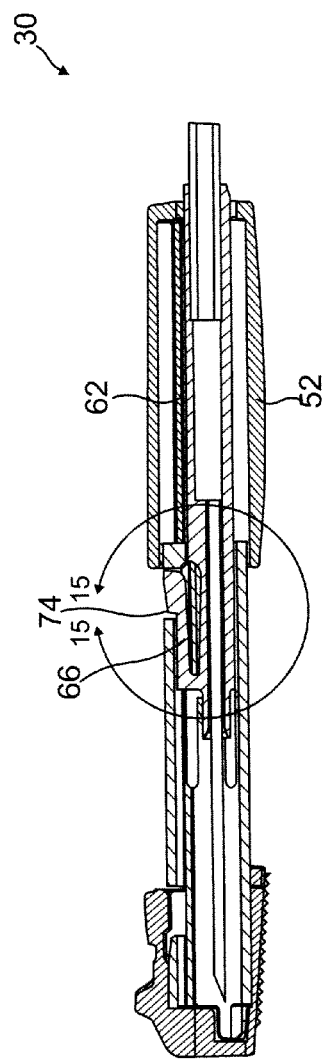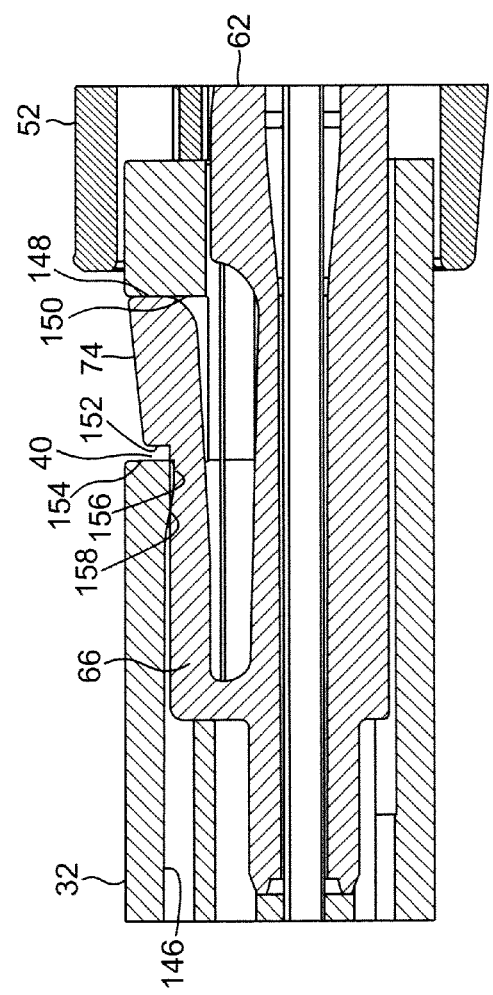
FIG. 14
FIG. 15

SAFETY NEEDLE ASSEMBLY AND METHODS

CROSS-REFERENCE TO RELATED APPLICATIONS

This is a US National phase application under 35 U.S.C. §371 of PCT Application No. PCT/US2010/042173, filed Jul. 15, 2010, which claims priority to U.S. Provisional Application No. 61/226,816, filed Jul. 20, 2009, the contents of each of which are expressly incorporated herein by reference.

BACKGROUND

The present invention relates to apparatus and methods for percutaneously infusing fluids to a body and/or withdrawing fluids from a body.

DESCRIPTION OF RELATED ART

Needle assemblies are commonly used to percutaneously infuse fluids to a body and/or withdraw fluids from a body. The needle assembly generally remains disposed in the vasculature while one or more assemblies are connected and disconnected to the assembly to complete the infusion/withdrawal process. Upon withdrawing the assembly from the vasculature, the sharp distal tip of the needle is exposed. It is disadvantageous to leave the tip exposed, as there is a risk that medical staff can accidentally prick themselves. This phenomenon is known as needlestick, and can transfer blood borne diseases.

SUMMARY

The various embodiments of the present safety needle assembly and methods have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description" one will understand how the features of the present embodiments provide advantages, which include reliable covering of the sharp needle tip.

One embodiment of the present safety needle assembly comprises an elongate body including a body wall defining an internal passageway. The assembly further comprises an elongate grip slidable along the exterior of the body between a distal position and a proximal position. The assembly further comprises an elongate needle holder disposed within the internal passageway and secured to the elongate grip, such that sliding movement of the grip induces sliding movement of the needle holder within the internal passageway. The assembly further comprises a needle extending distally from the needle holder and slidable with the needle holder within the internal passageway. The assembly further comprises a wing assembly secured to the body. The wing assembly includes first and second wings extending laterally in opposite directions from the body. The grip is slidable along the exterior of the body independently of the wing assembly. When the grip is in the distal position, the needle extends outward distally of the body such that a sharp distal tip of the needle is exposed, and when the grip is in the proximal position, the sharp distal tip of the needle is not exposed.

One embodiment of the present methods of shielding a needle in a safety needle assembly comprises grasping a grip of the assembly when the grip is in a distal position with respect to an elongate body of the assembly. The elongate body includes a body wall defining an internal passageway and including a distal opening in the body wall. The assembly further comprises a wing assembly secured to the elongate body. The wing assembly includes first and second wings extending laterally in opposite directions from the elongate body. The method further comprises depressing a release latch to thereby disengage a detent of the release latch from an edge of the distal opening in the body wall. The method further comprises sliding the grip along the exterior of the elongate body from the distal position toward a proximal position. The grip slides independently of the wing assembly. As the grip slides, it induces proximally directed sliding movement of a needle holder through the internal passageway. The needle holder draws a needle secured to the needle holder into the internal passageway. When the grip reaches the proximal position a sharp distal tip of the needle is not exposed.

In still yet another embodiment, there is provided a safety needle assembly comprising an elongate body having an internal passageway, an elongate grip having an internal passageway, an elongate needle holder having an internal passageway and a needle having a needle tip attached at a distal end of the elongate needle holder, and a wing assembly having an internal passageway. The elongate needle holder being disposed, at least in part, in the internal passageway of the wing assembly and in the internal passageway of the elongate body. The elongate body being disposed, at least in part, in the internal passageway of the elongate grip. In movement, the elongate grip being held in fixed relative movement with the elongate needle holder and the wing assembly being held in fixed relative movement with the elongate body. In activation, the elongate grip is movable relative to the wing assembly so that the needle and the needle tip are covered by the wing assembly and the elongate body in a protective position.

BRIEF DESCRIPTION OF THE DRAWINGS

The various embodiments of the present safety needle assembly and methods now will be discussed in detail with an emphasis on highlighting the advantageous features. These embodiments depict the novel and non-obvious safety needle assembly shown in the accompanying drawings, which are for illustrative purposes only. These drawings include the following figures, in which like numerals indicate like parts:

FIG. 14 is a cross-sectional right-side elevation view of the safety needle assembly of FIG. 8, taken through the line 14-14 in FIG. 11;

FIG. 15 is a detail, cross-sectional, right-side elevation view of a medial portion of the safety needle assembly of FIG. 8 indicated by the circle 15-15 in FIG. 14.

DETAILED DESCRIPTION

Figure 1:
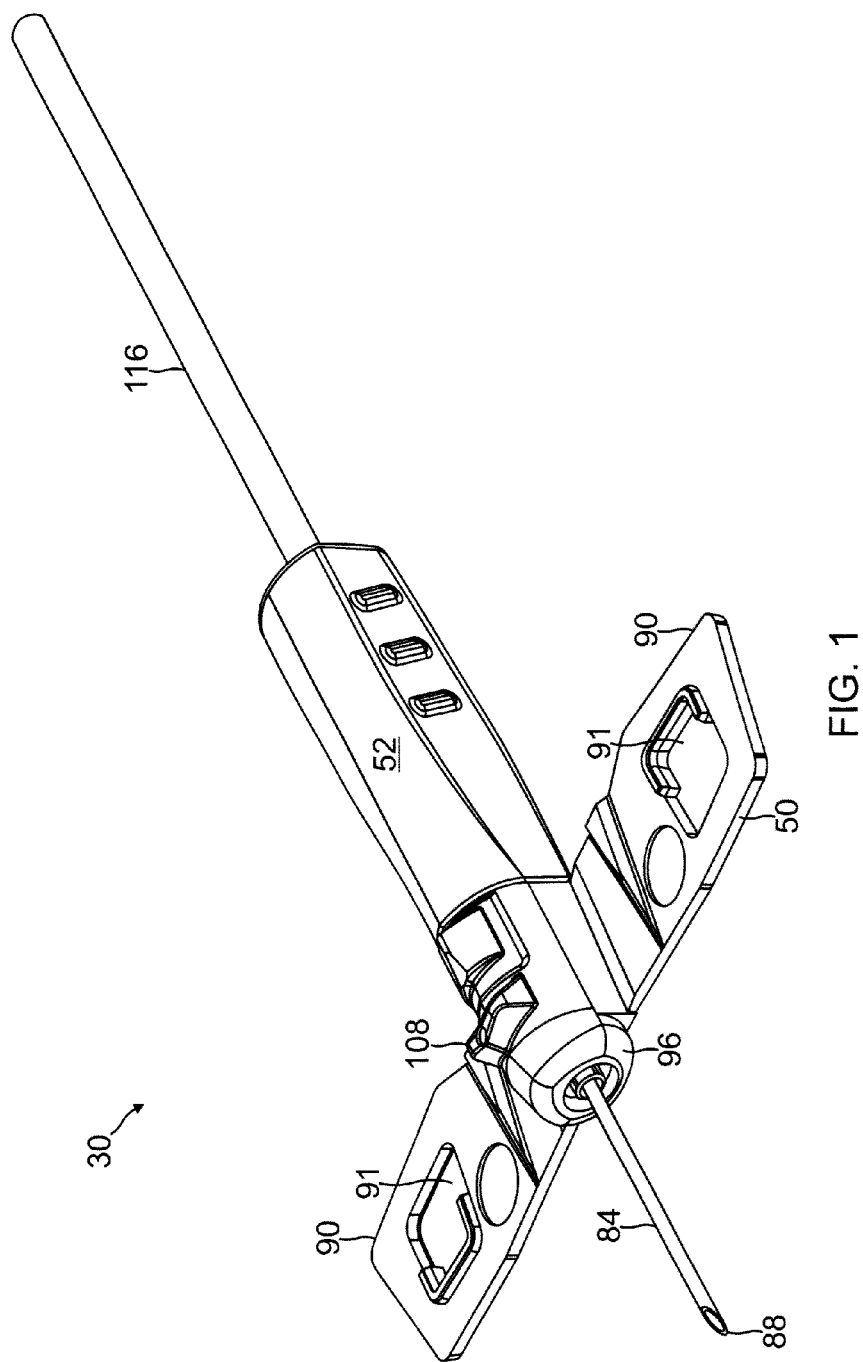
FIG. 1 is a front perspective view of one embodiment of the present safety needle assembly, showing a grip of the assembly in a distal position.

The following detailed description describes the present embodiments with reference to the drawings. In the drawings, reference numbers label elements of the present embodiments. These reference numbers are reproduced below in connection with the discussion of the corresponding drawing features.

The embodiments of the present safety needle assembly and methods are described below with reference to the figures. These figures, and their written descriptions, indicate that certain components of the apparatus are formed integrally, and certain other components are formed as separate pieces. Those of ordinary skill in the art will appreciate that components shown and described herein as being formed integrally may in alternative embodiments be formed as separate pieces. Those of ordinary skill in the art will further appreciate that components shown and described herein as being formed as separate pieces may in alternative embodiments be formed integrally. Further, as used herein the term integral describes a single unitary piece.

FIGS. 1-16 illustrate one embodiment of the present safety needle assembly 30. The assembly 30 is configured for use in drawing blood and/or infusing blood or other liquids. With reference to FIGS. 2 and 3, the assembly 30 comprises an elongate body 32. The body 32 is substantially cylindrical, and includes a body wall 34 defining an internal passageway 36. The body wall 34 includes a distal opening 38 and a proximal opening 40. Each of the openings 38, 40 is spaced a short distance from its respective end of the body 32. The function of the openings 38, 40 is described below.

Figure 11:
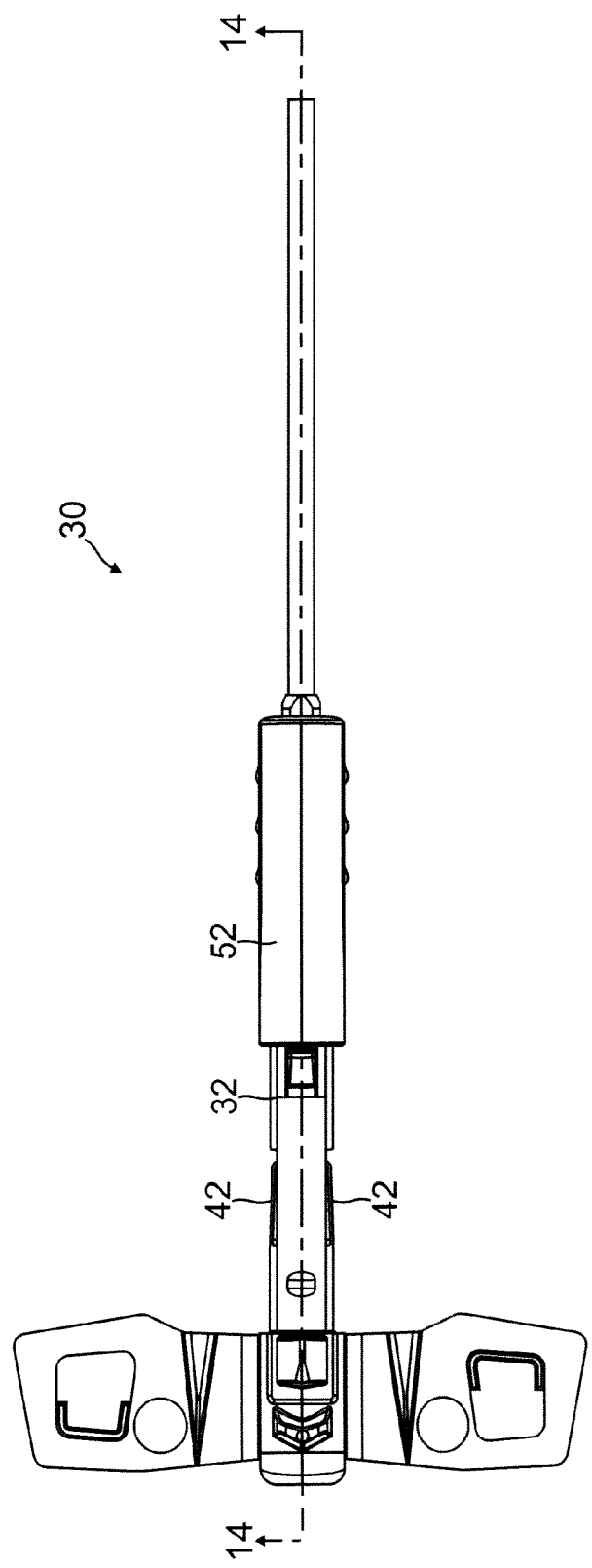
FIG. 11 is a top plan view of the safety needle assembly of FIG. 8.
Figure 12:
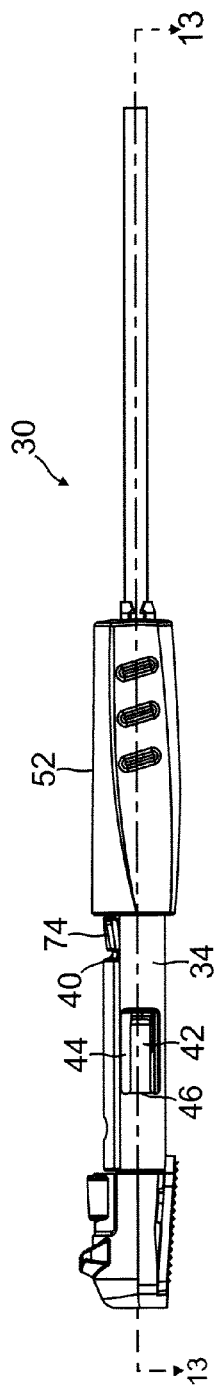
FIG. 12 is a right-side elevation view of the safety needle assembly of FIG. 8.

With reference to FIGS. 2 and 11-13, the body wall 34 further includes first and second opposed cantilevered fingers 42. With particular reference to FIG. 12, the fingers 42 are formed by creating a gap or cut-out 44 between each finger 42 and the body wall 34 along three sides of each finger 42. The fingers 42 are then cantilevered from the side along which they remain attached to the body wall 34. which in the illustrated embodiment is the distal side 46. The function of the fingers 42 is described below. With particular reference to FIG. 2, the body 32 further includes first and second distally extending tabs 48. The tabs 48 are spaced from one another by an arc less than 180°, and are located adjacent an underside of the body 32. The tabs 48 engage a wing assembly 50, as described in further detail below.

Figure 4:
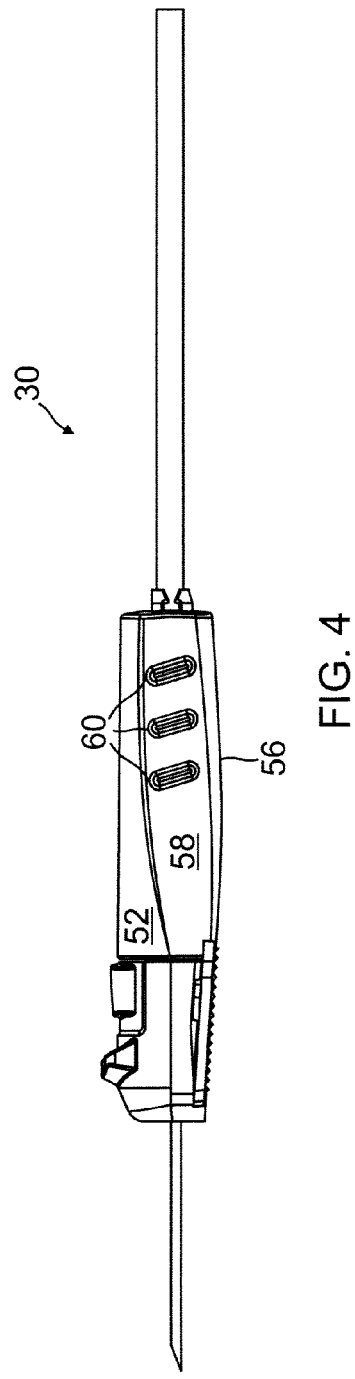
FIG. 4 is a right-side elevation view of the safety needle assembly of FIG. 1.

With reference to FIGS. 1-5, the assembly 30 further comprises an elongate grip 52 that is slidable along the exterior of the body 32. The grip 52 includes a smooth cylindrical inner surface 54 (FIG. 2), which is sized to snugly receive the exterior of the body 32 without creating significant sliding friction between the grip 52 and the body 32. With particular reference to FIGS. 2 and 4, the exterior of the grip 52 includes a substantially planar lower surface 56 and substantially planar side surfaces 58. The side surfaces 58 include raised bosses 60 that provide increased grip to the operator of the assembly 30.

Figure 6:
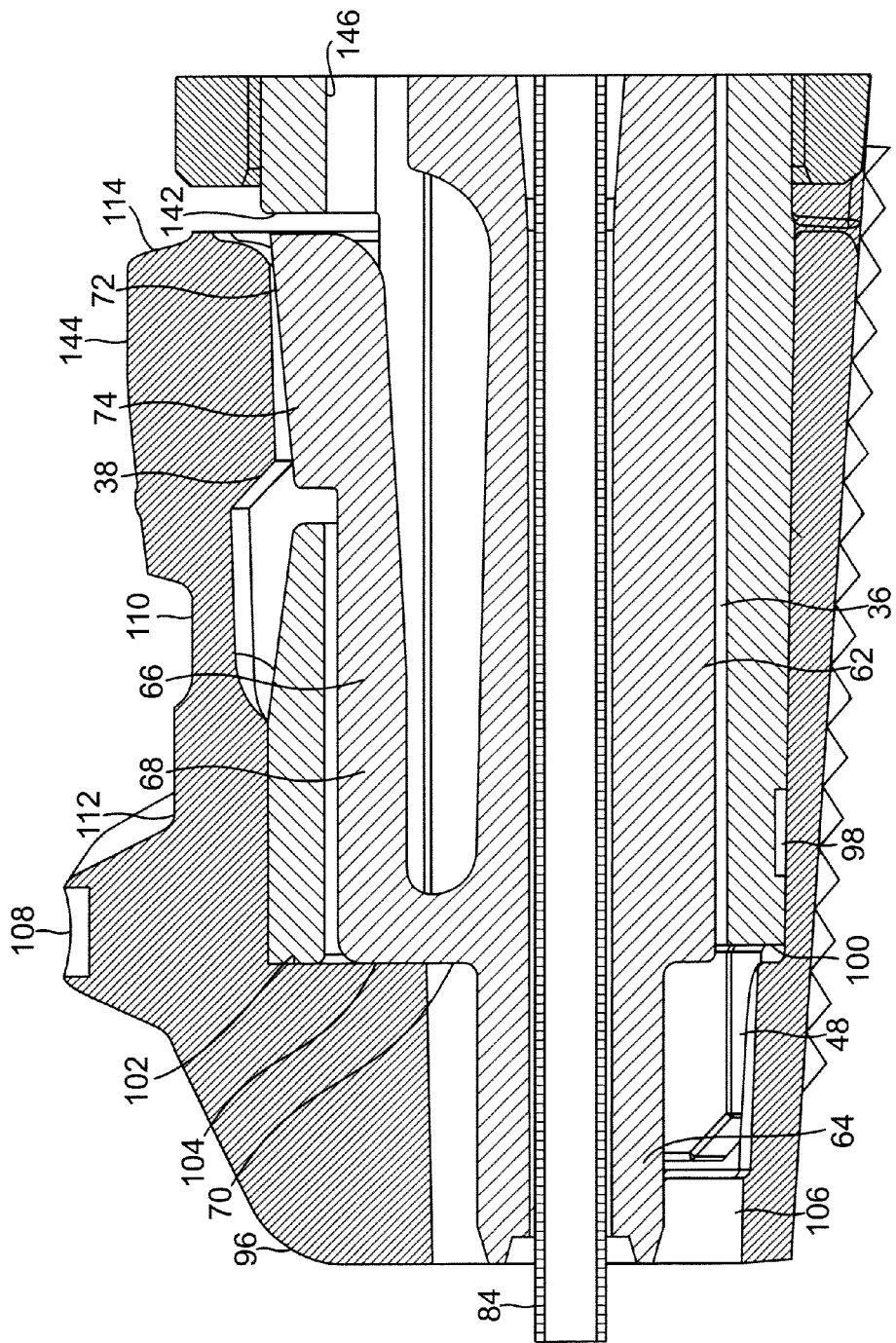
FIG. 6 is a detail, cross-sectional, right-side elevation view of a distal portion of the safety needle assembly of FIG. 1, indicated by the circle 6-6 in FIG. 3.

With reference to FIGS. 2, 3 and 6, the assembly 30 further comprises an elongate needle holder 62. The needle holder 62 is substantially cylindrical, and is slidably disposed at least partially within the internal passageway 36 in the body 32. At a distal end, a diameter of the needle holder 62 steps down and a relatively short cylindrical tip or glue well 64 extends distally from the needle holder 62. Just proximally of the tip 64, a release latch 66 extends along the needle holder 62. With particular reference to FIG. 6, the release latch 66 comprises a cantilevered aim 68 secured at its distal end 70 to the needle holder 62. The release latch 66 extends along and slightly away in a radial direction from the needle holder 62. A proximal end 72 of the release latch 66 includes a detent 74 on a surface opposite the needle holder 62. The detent 74 is configured to engage both of the distal and proximal openings 38, 40 in the body 32 to arrest sliding movement of the needle holder 62 and the grip 52 with respect to the body 32, as described in further detail below.

Figure 13:
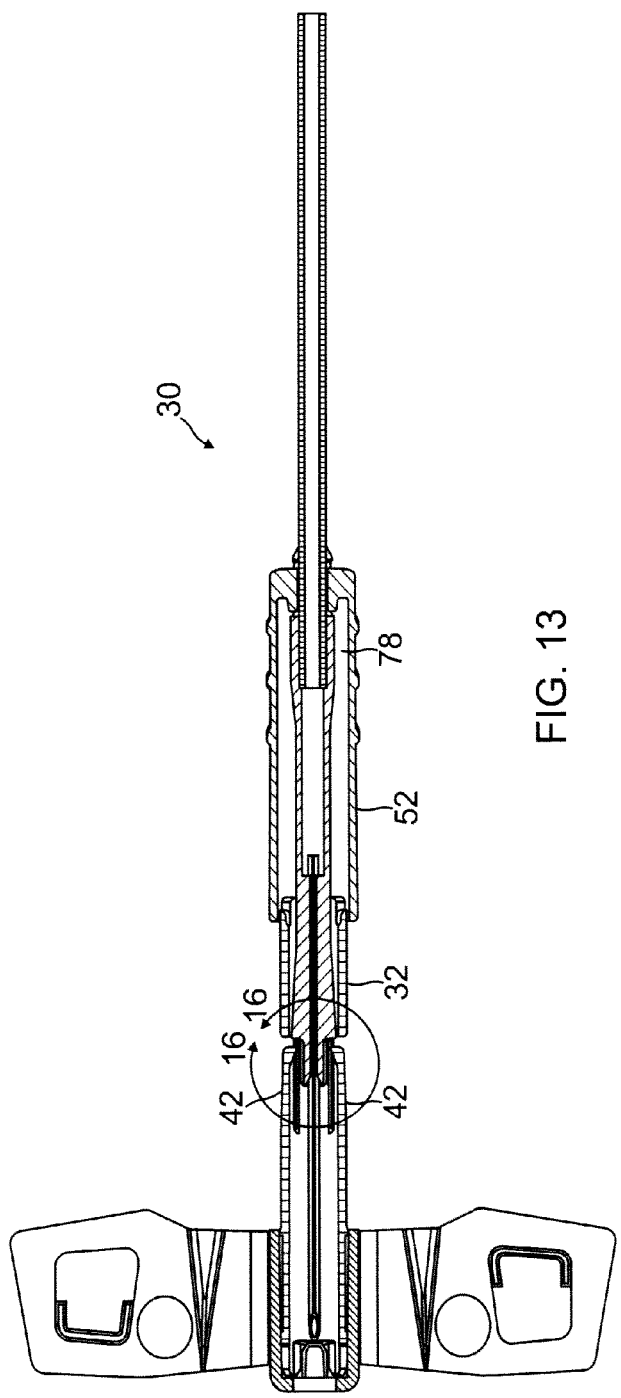
FIG. 13 is a cross-sectional top plan view of the safety needle assembly of FIG. 8, taken through the line 13-13 in FIG. 12.

With reference to FIG. 2, the needle holder 62 includes a medial region 76 having a first width, and a proximal region 78 having a second outside dimension that resembles an oval configuration, See e.g., FIGS. 3 and 13. A ramp section 80 marks the transition between the medial and proximal regions 76, 78. The needle holder 62 further includes a distal region 82 in which the width of the needle holder 62 tapers out to the distal end of the needle holder 62. The distal region 82, and its tapered sidewalls, engage the fingers 42 to bias them outward as the grip 52 and the needle holder 62 move proximally along the body 32, as described in further detail below.

With reference again to FIGS. 2 and 3, the assembly 30 further comprises a needle 84 extending distally from the needle holder 62. The needle 84 is fixed with respect to the needle holder 62 by known methods and slidable therewith within the internal passageway 36. The needle 84 includes a cannula 86 (FIG. 3), and a sharp distal tip 88.

Figure 2:
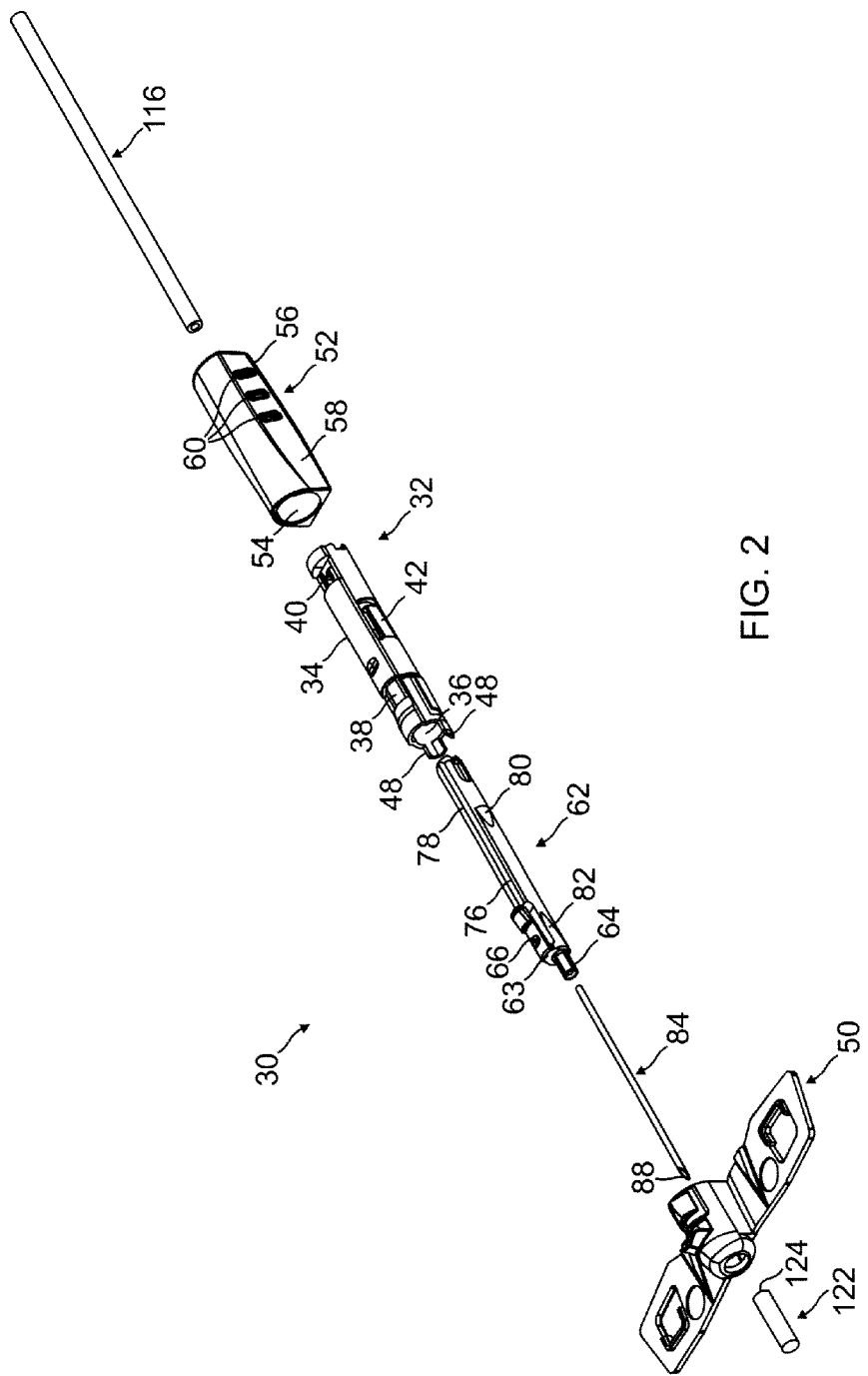
FIG. 2 is an exploded front perspective view of the safety needle assembly of FIG. 1.
Figure 3:
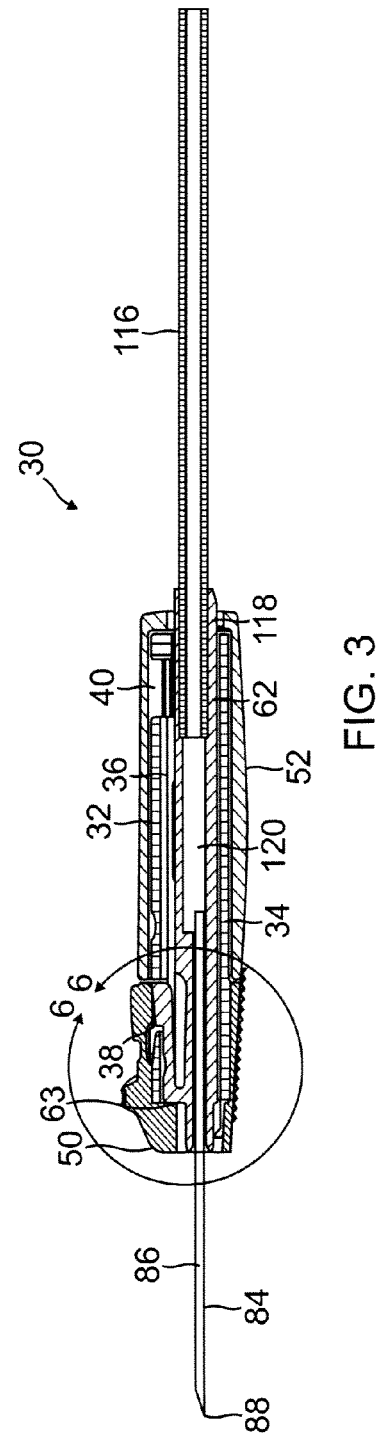
FIG. 3 is a cross-sectional right-side elevation view of the safety needle assembly of FIG. 1, taken through the line 3-3 in FIG. 5.
Figure 5:
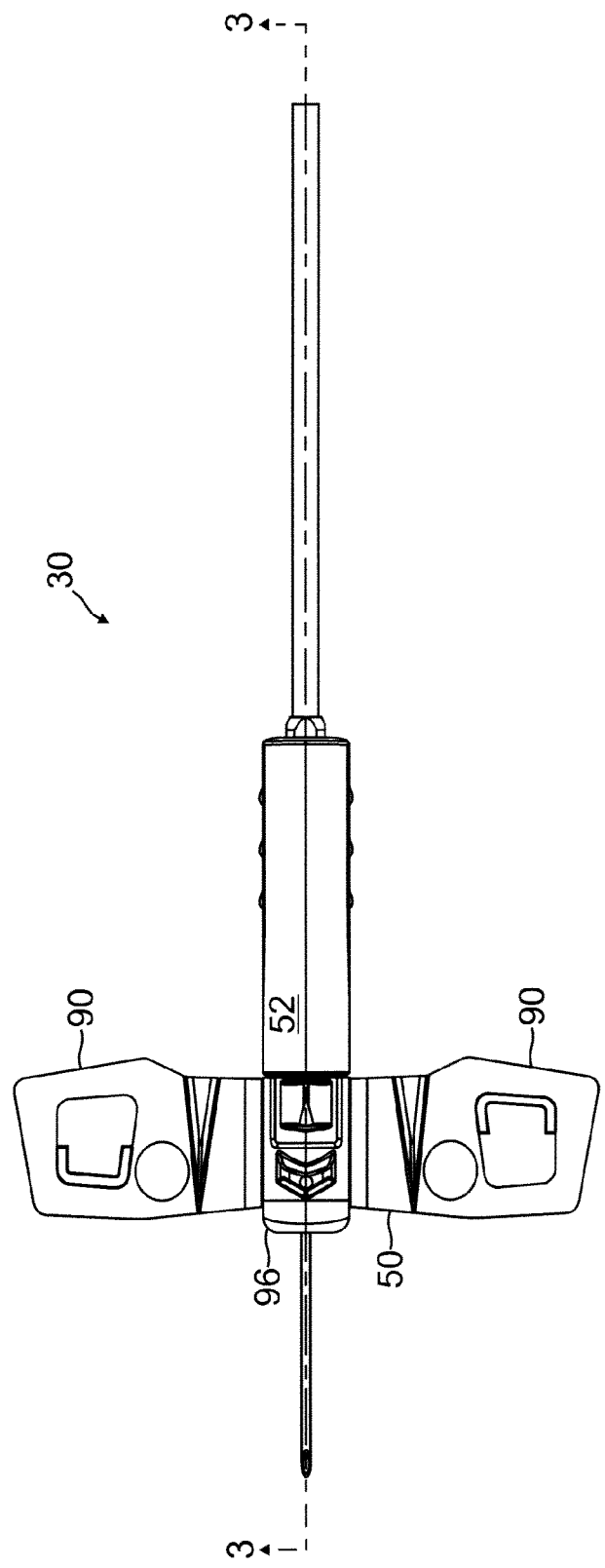
FIG. 5 is a top plan view of the safety needle assembly of FIG. 1.
Figure 7:
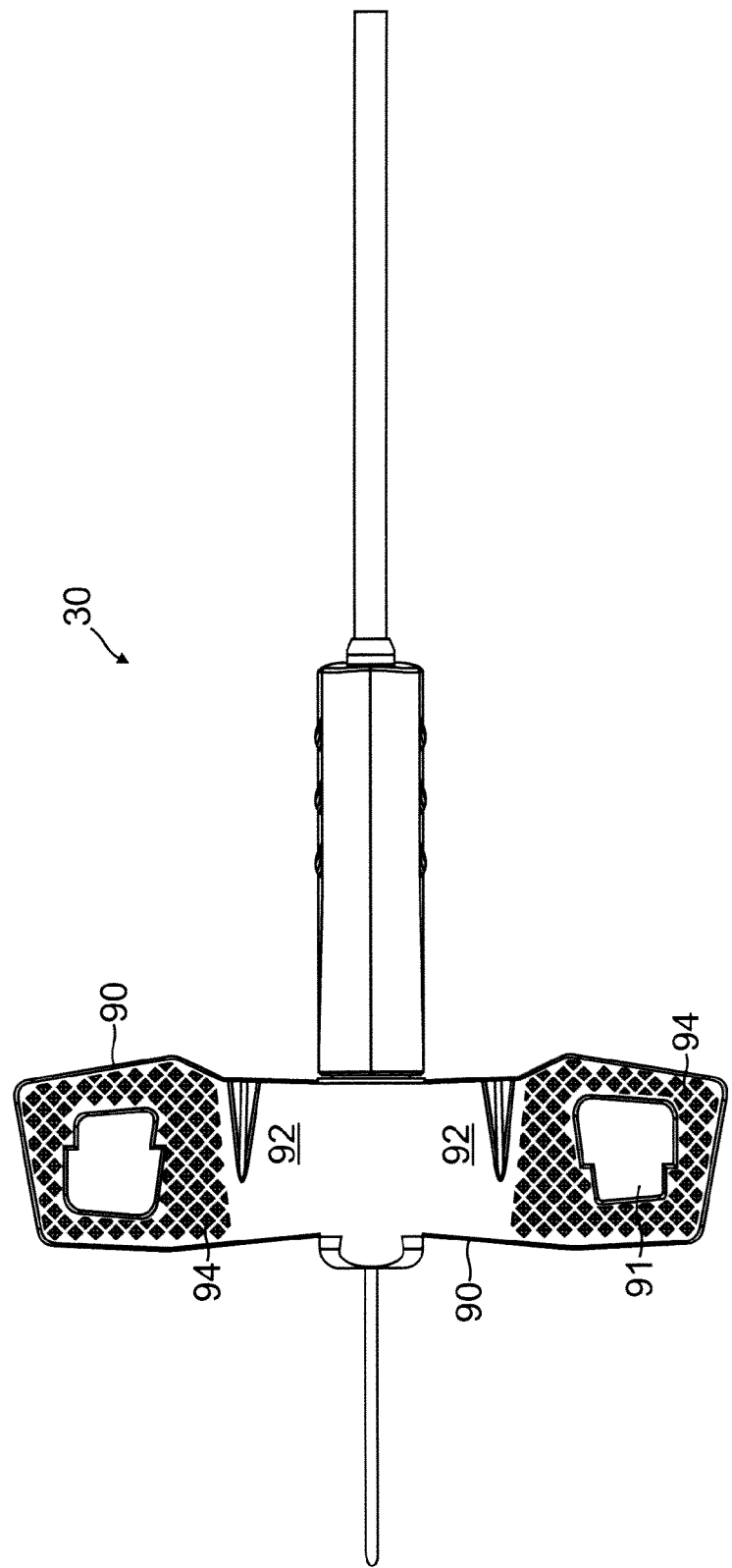
FIG. 7 is a bottom plan view of the safety needle assembly of FIG. 1.

With reference to FIGS. 1, 2 and 5, the assembly 30 further comprises a wing assembly 50. The wing assembly 50 is secured to the body 32 at a distal end thereof. With particular reference to FIGS. 1 and 5, the wing assembly 50 includes first and second wings 90 that extend laterally in opposite directions. The wings 90 are substantially planar and are constructed of a flexible material so that they can conform in to contoured body surfaces in the area of a blood draw/ infusion. In one embodiment, the wings 90 may be constructed of a suitable thermoplastic material. Tape (not shown) placed over the wings 90 secures the assembly 30 to the body. With reference to FIG. 7, an underside 92 of each wing may include texturing 94 to increase the ability of the wings 90 to grip the skin. An optional opening 91 on each wing 90 may be incorporated to facilitate securing the wings together.

With reference to FIGS. 1 and 5, the wing assembly 50 further comprises a housing 96 from which the wings 90 extend. With reference to FIG. 6, the housing 96 includes a generally cylindrical interior 98 configured to receive the distal end 100 of the body 32. The tabs 48 extending from the distal end 100 of the body 32 are received within mating slots (not shown) in the interior of the housing 96 for, among other things proper orientation and snap fit. Alternatively or in addition thereto, glue, adhesive, or solvent bonding may be used, such as by applying to the groove near the lead line for element 98 (FIG. 6), to more securely fix the wing assembly 50 to the body 32. The interior diameter of the housing 96 steps down toward its distal end, providing an annular shoulder 102 against which the distal end 100 of the body 32 and a distal annular shoulder 104 of the needle holder 62 abut. The distal end of the housing 96 includes an aperture 106 (FIG. 6) that receives the tip 64 of the needle holder 62 and through which the needle 84 extends.

With reference to FIG. 1, an upper surface of the housing 96 includes a raised or pushed off ridge 108 that extends laterally across a portion of the housing 96. The ridge 108 provides a gripping point for the operator. The raised surface also provides a convenient stop for a thumb or a finger for activating the safety feature, as described in further detail below. With reference to FIG. 6, just proximally of the ridge 108, the housing 96 includes a cantilevered arm 110 that is attached at its distal end 112 to the housing 96 and extends proximally. A proximal end 114 of the arm 110 includes an increased thickness. which acts as an activation button 144, as described in further detail below. In another embodiment, element 110 is a thin webbed section that expands three sides of the button 144 and is sufficiently rigid to provide a biasing force.

With reference to FIGS. 1-3, the assembly 30 is configured to receive intravenous (IV) tubing 116. With particular reference to FIG. 3, the tubing 116 is received partially within bore of a proximal region 118 of the needle holder 62, and extends proximally therefrom. The tubing 116 is in fluid communication with the interior 120 of the needle holder 62, which is in fluid communication with the cannula 86 of the needle 84. Blood flowing proximally through the needle 84 thus enters the interior 120 of the needle holder 62 and flows from there into the tubing 116. Those of ordinary skill in the art will appreciate that other apparatus instead of or in addition to the tubing 116 may be used to transfer blood to and/or from a body through the assembly 30. In another application, the assembly 30 is used for infusion or transferring fluid into a patient.

With reference to FIG. 2, in certain embodiments the assembly 30 may further comprise a disposable cap 122. After the assembly 30 is manufactured, for safety it may be shipped with the cap 122 covering the sharp distal tip 88 of the needle 84. The cap 122 is substantially cylindrical, and configured to cover the sharp distal tip 88 and the portion of the needle 84 extending outward from the wing assembly 50. A proximal end 124 of the cap 122 may include features (not shown) configured to secure the cap 122 to the housing 96 in a snap fit or alternatively a tight fit. When an operator prepares to use the assembly 30 to perform a blood draw or infusion, for example, he or she removes the cap 122 to expose the sharp distal tip 88 of the needle 84 and discards the cap 122.

Figure 8:
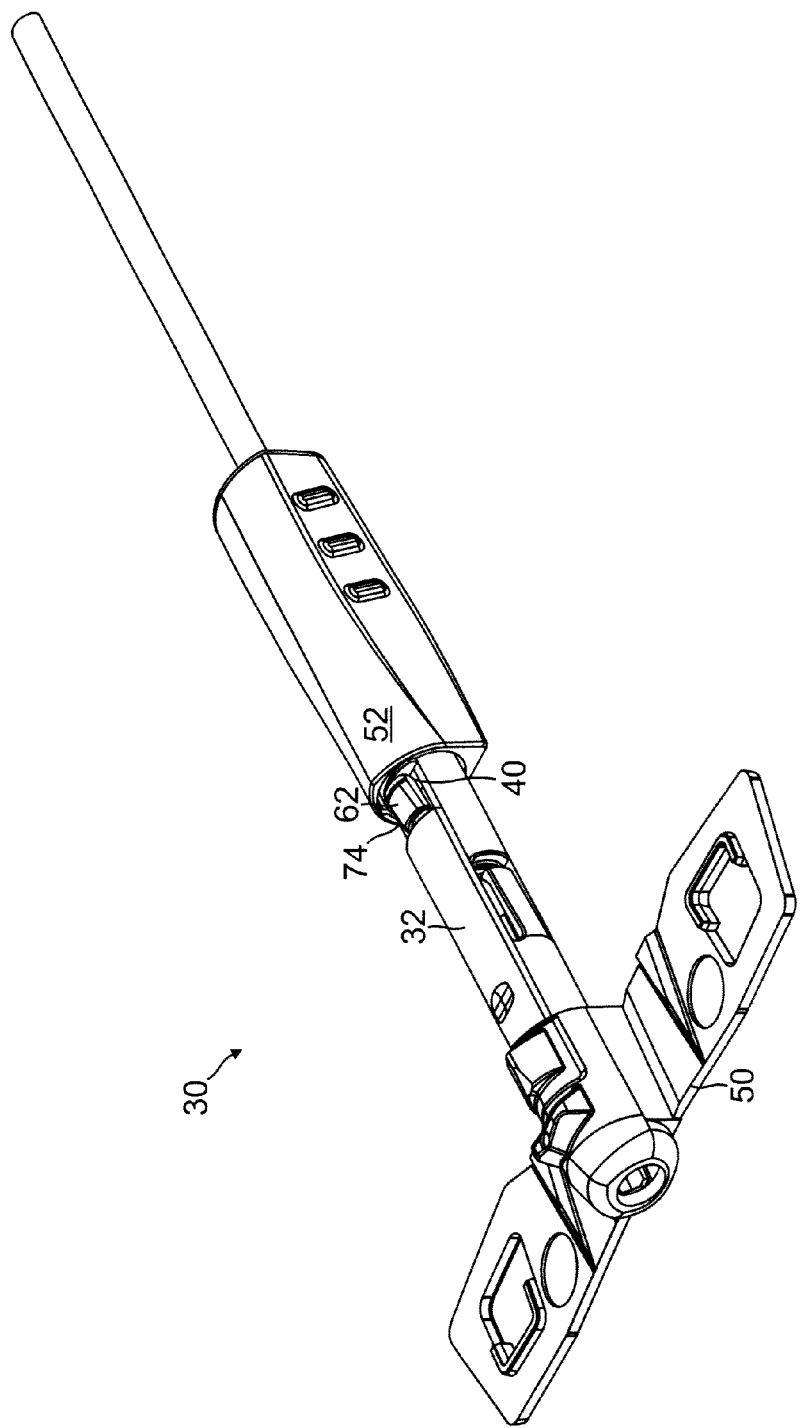
FIG. 8 is a front perspective view of the safety needle assembly of FIG. 1, showing a grip of the assembly in a proximal position.

With reference to FIGS. 1 and 8, the grip 52 is slidable along the exterior of the body 32 between a distal position (FIG. 1) and a proximal position (FIG. 8). The two positions may also be referred to as a needle extended position and a needle retracted position. The two positions may also sometime be referred to as a ready position and a shielded, covered, or protected position. The grip 52 slides independently of the wing assembly 50, which remains fixed to the distal end of the body 32. However, the needle holder 62 slides with the grip 52, since the two are secured to one another, as described below.

Figure 9:
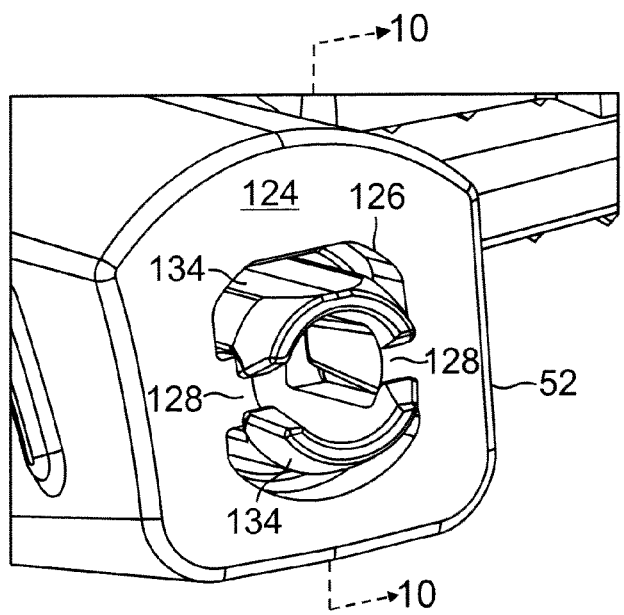
FIG. 9 is a detail rear perspective view of the safety needle assembly of FIG. 1.
Figure 10:
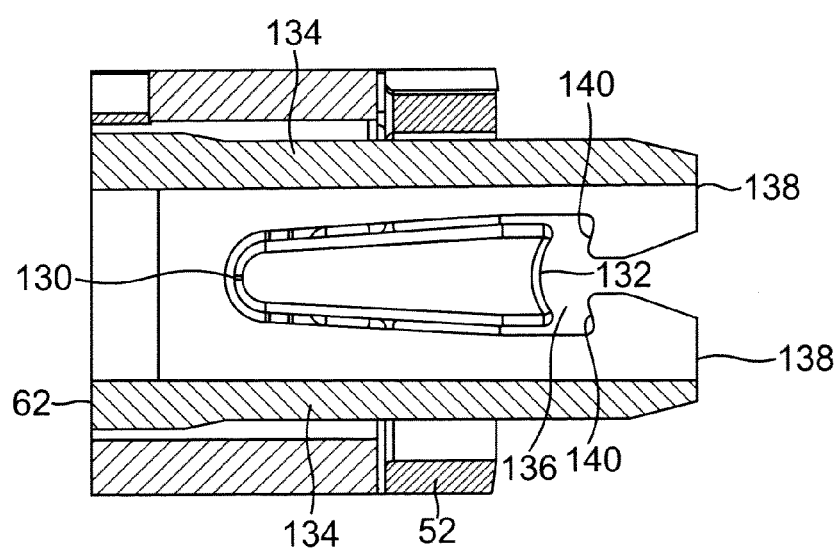
FIG. 10 is a detail, cross-sectional, right-side elevation view of a proximal portion of the safety needle assembly of FIG. 1, taken through the line 10-10 in FIG. 9.

FIGS. 9 and 10 illustrate the engagement of the needle holder 62 with the grip 52. In particular, as shown in FIG. 9, a proximal end wall 124 of the grip 52 includes an aperture 126. First and second tabs 128 extend inwardly from opposite edges of the aperture 126. With reference to FIG. 10, in profile each of the tabs 128 includes a rounded distal end 130 and a tapered height that increases in the distal to proximal direction. A proximal face 132 of each tab 128 is concave. The interior wall surface of each tab is likewise curved but may optionally be flat or include surface features.

With reference again to FIGS. 9 and 10, a proximal end of the needle holder 62 includes first and second opposed cantilevered arms 134. With particular reference to FIG. 10, a space 136 between the arms 134 has a shape complimentary to the shape of the tabs 128, but larger so that the tabs 128 can be received in the spaces 136 between the arms 134. The tab 128 should only move minimally within the spaces 136. Among other things, as the tabs 128 are trapped in the space 136 between the cantilevered arms 134, the needle holder 62 and the grip part 52 are configured to move in fixed relations to one another and relative to the wings 90 and/or the elongated body 32, which is positioned coaxially over the needle holder 62.

Adjacent their proximal ends 138, the space 136 between the arms 134 gets narrower, so that each arm 134 includes first and second opposed retaining tabs 140. The retaining tabs 140 on either arm 134 are separated from one another by an arc of less than 180°. Proximally of the retaining tabs 140, the space 136 between the arms 134 again gets wider. The distance between opposed retaining tabs 140 on the arms 134 is less than the height of the tabs 128 at their proximal ends 132. However, a distance between the arms 134 at their proximal ends 138 is greater than the height of the tabs retaining tabs 140 at their distal ends 130. Thus, when the assembly 30 is manufactured the needle holder 62 is secured to the grip 52 by advancing the needle holder 62 proximally through the interior of the grip 52 until the proximal ends 138 of the anus 134 ride up and over the tabs 128. As the aims 134 advance along the tabs 128, the increasing height of the tabs 128 forces the arms 134 apart, until the retaining tabs 140 pass over the proximal ends of the tabs 128. at which point the arms 134 snap back to their non-flexed state, as shown in FIGS. 9 and 10. In this configuration, the arms 134 surround the tabs 128, and the retaining tabs 140 resist disengagement of the needle holder 62 from the grip 52. Sliding movement of the grip 52 along the exterior of the body 32 thus induces sliding movement of the needle holder 62 within the internal passageway 36 of the body 32, as described in further detail below.

When the grip 52 is in the distal position of FIG. 1, the needle 84 extends outward distally of the body 32 such that the sharp distal tip 88 of the needle 84 is exposed. This configuration is referred to as the ready-to-use position. When the grip 52 is in the proximal position of FIG. 8, the sharp distal tip 88 of the needle 84 is within the assembly 30 so that it is not exposed. The operator thus moves the grip 52 to the proximal position upon completion of a blood draw or infusion using the assembly 30. Doing so reduces the likelihood that the needle 84 will accidentally stick the operator or anybody else. In another embodiment, a coil spring is incorporated to propel the grip to the proximal position when activated. When incorporated, the coil spring may be positioned between the base or shoulder 63 (FIG. 2) on the elongated needle holder 62 and a base or shoulder (not shown) on the wing assembly housing 50 (FIG. 3), such as by extending the housing distally and forming a shoulder.

The assembly 30 includes features that resist accidental sliding movement of the grip 52 along the exterior of the body 32 when the grip 52 is in either the distal position or the proximal position. FIG. 6 shows the configuration inside the housing 96 when the grip 52 is in the distal position. The shoulder 102 on the interior of the housing 96 forms a barrier for the distal annular shoulder 104 of the needle holder 62. The shoulders 102, 104 thus resist distal movement of the needle holder 62 within the internal passageway 36 of the body 32. Further, when the grip 52 and the needle holder 62 are in the distal position, the detent 74 on the release latch 66 is disposed within the distal opening 38 in the body 32. A proximal face 142 of the distal opening 38 forms a barrier for the detent 74, thus resisting proximal movement of the needle holder 62 within the internal passageway 36 of the body 32. Since the grip 52 and the needle holder 62 are secured to one another at their proximal ends, the engagement of the detent 74 and the distal opening 38 also resists proximal movement of the grip 52 along the exterior of the body 32.

With continued reference to FIG. 6. the cantilevered arm 110 of the wing assembly 50 extends over the distal opening 38. The thickened proximal end 114 of the arm 110 abuts the detent 74. Digital pressure applied to the proximal end is transmitted to the detent 74. The proximal end 114 thus acts as an activation button 144. When the operator depresses the activation button 144, the cantilevered arm 110 flexes toward the needle holder 62, which in turn causes the cantilevered release latch 66 of the needle holder 62 to also flex toward the needle holder 62. When the latch 66 has flexed sufficiently that the detent 74 is at an elevation below the proximal surface 142 of the distal opening 38, the operator can slide the grip 52 and the needle holder 62 proximally along the outside of the body 32. An interior surface 146 of the body 32 is smooth in the region between the distal opening 38 and the proximal opening 40. Thus, as the needle holder 62 slides proximally, the detent 74 will slide smoothly along the interior surface 146 as the cantilevered release latch 66 biases it into contact with the interior surface 146.

With reference to FIGS. 12, 14 and 15. when the grip 52 and the needle holder 62 are in the proximal position, the detent 74 on the release latch 66 is located in the proximal opening 40. With particular reference to FIG. 15, engagement of a proximal surface 148 of the detent 74 with a proximal surface 150 of the proximal opening 40 resists proximal movement of the needle holder 62 and the grip 52. Engagement of a distal surface 152 of the detent 74 with a distal surface 154 of the proximal opening 40 resists distal movement of the needle holder 62 and the grip 52. The detent 74 and the proximal opening 40 thus maintain the needle holder 62 and the grip 52 in the proximal position in which the sharp distal tip 88 of the needle 84 is safely disposed within the assembly 30.

With continued reference to FIG. 15, as the needle holder 62 approaches the proximal position, the cantilevered release latch 66 is biased inwardly as the inner surface 146 of the body 32 bears against the detent 74. When the detent 74 reaches the proximal opening 40, the bias in the latch 66 causes the detent 74 to pop outwardly and into the proximal opening 40. When it does so, a surface of the latch 66 adjacent the detent 74 impacts an interior edge 156 of the distal surface 154 of the proximal opening 40. The impact generates a clicking noise, which provides an audible signal to the operator that the detent 74 is safely within the proximal opening 40 and the sharp distal tip 88 of the needle 84 is safely stowed inside the assembly 30. Thus, an aspect of the present invention is the inclusion of an audio feedback upon engagement of a cantilevered arm to an opening during retraction of a needle inside an elongated body 32 and wing assembly 50 combination.

In the illustrated embodiment. the wall thickness of the body 32 begins to increase from a point adjacent the proximal opening 40 to a maximum thickness at the distal surface 154. The inner surface 146 thus provides a ramp 158 that the detent 74 rides up and over before entering the proximal opening 40. The ramp 158 generates an increasing bias in the latch 66 just prior to the detent 74 reaching the proximal opening 40. The increasing bias causes the latch 66 to pop outwardly with greater force when the detent 74 reaches the proximal opening 40. The detent 74 is thus more likely to properly enter the opening 40, rather than sliding underneath it. Also, because the ramp 158 extends toward the needle holder 62, it increases the likelihood of contact between the inner edge 156 and the latch 66, enhancing the sound made by the impact.

Figure 16:
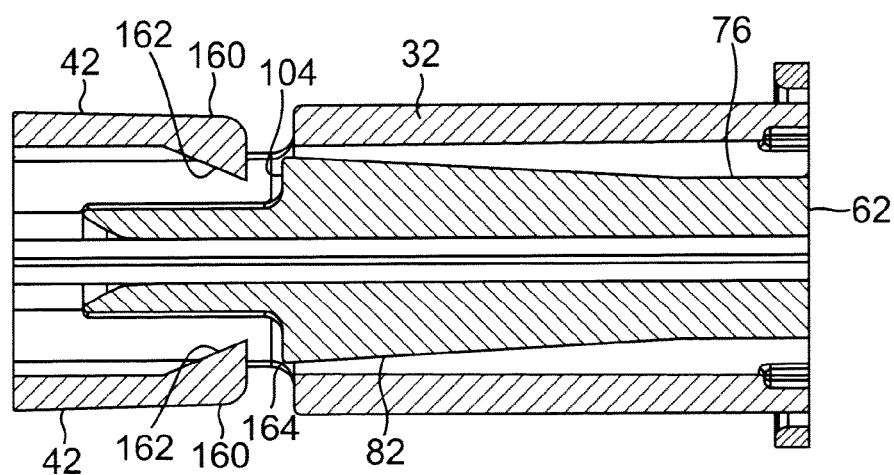
FIG. 16 is a detail, cross-sectional, top plan view of a medial portion of the safety needle assembly of FIG. 8, indicated by the circle 16-16 in FIG. 13.

With reference to FIGS. 11, 13 and 16, the cantilevered fingers 42 on the body 32 also restrict the distal movement of the grip 52 and the needle holder 62 with respect to the body 32. With particular reference to FIG. 16, at a proximal end 160 each finger 42 includes a steadily increasing wall thickness so that an interior surface 162 of the finger 42 tapers inwardly toward the proximal end 160. Along the medial region 76, a width of the needle holder 62 is substantially constant. Further, the width of the needle holder 62 in this region 76 is less than or substantially equal to a spacing between the proximal ends 160 of the fingers 42 when they are not flexed, as shown in FIG. 16. Thus, as the needle holder 62 moves from the distal position toward the proximal position, the fingers 42 do not contact the needle holder 62, or slide easily against the sidewalls of the needle holder 62 in a non-flexed state. However, a width of the needle holder 62 increases steadily in the distal region 82 to a maximum thickness at the distal end 164. Thus, when the fingers 42 reach this region 82, they begin to flex outwardly as they ride up and over the increasing thickness of the needle holder 62. When, or shortly before, the needle holder 62 reaches the proximal position, the fingers 42 snap back toward one another as the maximum width at the distal end 164 of the needle holder 62 passes between them. With particular reference to FIG. 16, the fingers 42 thus occupy the return path of the needle holder 62, resisting its movement back toward the distal position. The distal annular shoulder 104 of the needle holder 62 will encounter the distal ends 160 of the fingers 42 if the operator attempts to slide the grip 52 distally away from the proximal position.

In use, an operator of the present safety needle assembly 30 would move the needle 84 into the stowed position of FIG. 8 after using the assembly 30 to perform a blood draw or infusion. To do so, he or she begins with the assembly 30 in the ready to use configuration of FIG. 1. He or she grasps the wing assembly 50 with one hand, and the grip 52 with the other hand. While applying pressure to the activation button 144, the operator pulls on the grip 52 to move it proximally along the body 32. The pressure applied to the activation button 144 is transmitted to the detent 74 to flex the release latch 66 of the needle holder 62 and move the detent 74 out of the distal opening 38. The operator continues sliding the grip 52 proximally along the body 32 until the detent 74 pops into the proximal opening 40, at which point the operator hears a click and the needle 84 is safely stowed. The grip 52 and the needle holder 62 slide independently of the wing assembly 50, which is not slidable with respect to the body 32. While pulling on the grip 52, the operator may rest a finger on the ridge 108 in order to apply a distally directed force to the wing assembly 50 to counter the proximally directed force applied to the grip 52. However, the assembly is configured to conveniently be used with one hand. For example, while button 144 is activated by an index finger, the grip 52 is pulled by a thumb and at least one other finger.

In the present safety needle assembly 30, the various components described above may be made from any suitable material that is durable and rigid or semi-rigid, except for the wings 90, which are preferably flexible as described above. Example materials include acrylonitrile butadiene styrene (ABS), polyethylene (PE), polypropylene (PP) and other suitable thermoplastic materials.

The above description presents the best mode contemplated for carrying out the present safety needle assembly and methods, and of the manner and process of making and using it, in such full, clear, concise, and exact terms as to enable any person skilled in the art to which it pertains to make and use this safety needle assembly. This safety needle assembly is, however, susceptible to modifications and alternate constructions from that discussed above that are fully equivalent. Consequently, this safety needle assembly is not limited to the particular embodiments disclosed. On the contrary, this safety needle assembly covers all modifications and alternate constructions coming within the spirit and scope of the safety needle assembly as generally expressed by the following claims, which particularly point out and distinctly claim the subject matter of the safety needle assembly.

What is claimed is:

1. A safety needle assembly, comprising:
an elongate body including a body wall defining an internal passageway and having an exterior;
a grip part having an internal passageway slidable along the exterior of the body between a needle exposed position and a needle covered position;
an elongate needle holder disposed within the internal passageway of the elongate body and removeably secured to the grip part, such that sliding movement of the grip part induces sliding movement of the needle holder within the internal passageway;
a needle comprising a needle tip extending distally from the needle holder and slidable with the needle holder within the internal passageway of the elongate body;
a wing assembly secured to a distal end of the elongate body, the wing assembly including first and second wings extending laterally in opposite directions and a fixed distal end opening defining a cover end for covering the needle tip in the needle covered position;
wherein the grip part is slidable along the exterior of the body independently of the wing assembly; and
wherein the safety needle assembly is without a biasing spring such that movement of the needle tip inside the cover end of the wing assembly is without any biasing spring force.

2. The safety needle assembly of claim 1, wherein the elongate body includes a distal opening in the body wall spaced from a distal end opening and a proximal opening in the body wall spaced from a proximal end opening.

3. The safety needle assembly of claim 2, wherein the needle holder includes a detent that is biased in a radial direction away from the needle.

4. The safety needle assembly of claim 3, wherein a leaf spring is connected to biases the detent.

5. The safety needle assembly of claim 3, wherein when the grip part is in the needle exposed position the detent on the needle holder is disposed in the distal opening of the elongate body, and when the grip part is in the needle covered position the detent is disposed in the proximal opening of the elongate body.

6. The safety needle assembly of claim 1, further comprising a first internal detent securing the needle holder to the elongate body and an outer release tab disposed over the internal detent for releasing the internal detent to enable movement of the needle to the needle covered position.

7. The safety needle assembly of claim 1, wherein the needle holder and the grip part engage one another at a proximal end of each.

8. The safety needle assembly of claim 1, wherein the grip part comprises a plurality of raised bosses on the exterior thereof.

9. The safety needle assembly of claim 1, further comprising a tube disposed partly within the needle holder and extending proximally from the assembly.

10. The safety needle assembly of claim 1, wherein the body further comprises at least one cantilevered finger that is biased outwardly by the needle holder when the grip part is in the needle exposed position.

11. The safety needle assembly of claim 10, wherein as the grip part moves toward the needle covered position the finger is released so that a portion of the finger extends into the internal passageway to resist movement of the grip part and the needle holder toward the needle exposed position.

12. A method of shielding a needle in a safety needle assembly, the method comprising:
grasping a grip having an internal passageway having an elongate body disposed therein, the elongate body including a body wall defining an internal passageway and including a distal opening in the body wall, the assembly further comprising a wing assembly secured to the elongate body, the wing assembly including first and second wings extending laterally in opposite directions from the elongate body;
depressing a release latch to thereby disengage a detent of the release latch from an edge of the distal opening in the body wall; and
sliding the grip along the exterior of the elongate body from a distal position with respect to the elongate body toward a proximal position with respect to the elongate body;
wherein the grip slides independently of the wing assembly; and
wherein as the grip slides it induces proximally directed sliding movement of a needle holder through the internal passageway, the needle holder drawing a needle secured to the needle holder into the internal passageway, and when the grip reaches the proximal position a sharp distal tip of the needle is not exposed.

13. The method of claim 12, wherein the elongate body further comprises a proximal opening in the body wall spaced from a proximal end opening.

14. The method of claim 13, wherein when the grip reaches the proximal position the detent moves into the proximal opening.

15. The method of claim 14, wherein the detent disposed in the proximal opening resists distally directed movement of the grip along the exterior of the elongate body from the proximal position.

16. The method of claim 12, wherein depressing the release latch comprises applying pressure to a cantilevered button extending from the wing assembly.

17. The method of claim 12, further comprising releasing at least one cantilevered finger of the elongate body as the body moves toward the proximal position so that a portion of the finger extends into the internal passageway and resists movement of the grip and the needle holder toward the distal position.

18. A safety needle assembly comprising:
an elongate body having an internal passageway;
an elongate grip having an internal passageway;
an elongate needle holder having an internal passageway and a needle having a needle tip attached at a distal end of the elongate needle holder;

a wing assembly having an internal passageway;

the elongate needle holder being disposed, at least in part, in the internal passageway of the wing assembly and in the internal passageway of the elongate body;

the elongate body being disposed, at least in part, in the internal passageway of the elongate grip;

the elongate grip being held in fixed relative movement with the elongate needle holder;

the wing assembly being held in fixed relative movement with the elongate body; and wherein the elongate grip is movable relative to the wing assembly so that the needle and the needle tip are covered by the wing assembly and the elongate body in a protective position.

19. A safety needle assembly, comprising:

an elongate body having a distal opening;

a grip part slidable with respect to the elongate body between a needle exposed position and a needle covered position;

an elongate needle holder disposed in the elongate body and slidable with respect to the elongate body;

a needle extending distally from the needle holder and slidable with the needle holder;

a wing assembly comprising a bore positioned over and secured to a distal end of the elongate body, the wing assembly including first and second wings extending laterally in opposite directions; and an internal detent securing the needle holder to the elongate body and an outer release tab separately formed from the internal detent and disposed externally of the internal detent, said outer release tab in abutting contact with the internal detent to release the internal detent when the outer release tab is pressed.

20. The safety needle assembly of claim 19, wherein the assembly is without a biasing spring such that movement of the needle tip inside the wing assembly is without any biasing spring force.

21. The safety needle assembly of claim 19, wherein the needle holder is secured to the grip part such that sliding movement of the grip part induces sliding movement of the needle holder.

22. The safety needle assembly of claim 19, wherein the grip part is slidable along the exterior of the body independently of the wing assembly.

23. The safety needle assembly of claim 19, wherein the internal detent is formed on the elongate needle holder.

24. The safety needle assembly of claim 19, wherein the elongate body has an internal passageway and the grip part has an internal passageway.

25. The safety needle assembly of claim 19, wherein the wing assembly has the outer release tab formed therewith.

26. The safety needle assembly of claim 24, wherein the wing assembly has the outer release tab formed therewith.

27. The safety needle assembly of claim 18, wherein at least part of the elongate body is disposed inside the internal passageway of the wing assembly.

28. The safety needle assembly of claim 18, wherein the wing assembly has an outer release tab for pushing an internal detent located on the elongate needle holder.

29. The safety needle assembly of claim 18, further comprising an internal detent disposed in an opening formed on a body of the elongate body.

30. The safety needle assembly of claim 18, wherein the internal detent is located on a leaf spring formed with the elongate needle holder.

* * * * *

UNITED STATES PATENT AND TRADEMARK OFFICE
CERTIFICATE OF CORRECTION

PATENT NO.        : 9,095,651 B2                                                                 Page 1 of 1
APPLICATION NO.   : 13/381829
DATED             : August 4, 2015
INVENTOR(S)       : Chai Wayne Ng et al.

It is certified that error appears in the above-identified patent and that said Letters Patent is hereby corrected as shown below:

In the Specification

In column 3, line 58, delete "wall 34." and insert -- wall 34, --, therefor.

In column 4, line 51, after "conform" delete "in".

In column 6, line 35, delete "anus" and insert -- arms --, therefor.

In column 6, line 39, delete "128." and insert -- 128, --, therefor.

In column 7, line 16, delete "FIG. 6." and insert -- FIG. 6, --, therefor.

In column 7, line 35, delete "15." and insert -- 15, --, therefor.

In column 7, line 66, delete "embodiment." and insert -- embodiment, --, therefor.

Signed and Sealed this
Third Day of May, 2016

Michelle K. Lee
*Director of the United States Patent and Trademark Office*